United States Patent
Fries

(10) Patent No.: US 6,593,575 B2
(45) Date of Patent: Jul. 15, 2003

(54) SYSTEM AND METHOD FOR ASCRIBING TIMES TO EVENTS IN A MEDICAL IMAGING SYSTEM

(75) Inventor: Mark D. Fries, Williams Bay, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 166 days.

(21) Appl. No.: 09/682,498

(22) Filed: Sep. 7, 2001

(65) Prior Publication Data

US 2003/0047686 A1 Mar. 13, 2003

(51) Int. Cl.⁷ ............................................. G01T 1/1666
(52) U.S. Cl. .............................. 250/363.03; 250/363.02
(58) Field of Search ....................... 250/363.03, 363.02, 250/234, 205, 559.06, 559.22, 216, 559.1, 208.1, 227.12; 356/4.02

(56) References Cited

U.S. PATENT DOCUMENTS

| | | | |
|---|---|---|---|
| 4,994,695 A | | 2/1991 | Bazes |
| 5,241,181 A | | 8/1993 | Mertens et al. |
| 5,272,343 A | | 12/1993 | Stearns |
| 6,144,034 A | * | 11/2000 | Scharf et al. ................ 250/369 |
| 6,169,285 B1 | * | 1/2001 | Petrillo et al. ............... 250/369 |
| 6,403,960 B1 | * | 6/2002 | Wellnitz et al. ......... 250/363.09 |
| 6,410,920 B1 | * | 6/2002 | Shao et al. ............. 250/363.04 |
| 2001/0000820 A1 | | 5/2001 | Keeth et al. |

OTHER PUBLICATIONS

Kleinfelder, Stuart; Majors, T.J.; Blumer, K.A.; Farr, W.; Manor, Ben; MTD–132–A New Sub–Nanosecond Multi–hit CMOS Time–to–Digitial Converter, IEEE. Transactions On Nuclear Science, vol. 38, No. 2, Apr. 1991; pp. 97–101.

Dhawan, Satish K., Time Measurement With A Multiphase Clock, IEEE Transactions On Nuclear Science, vol. NS–30, No. 1, Feb. 1983, pp. 293–296.

Legrele, C. and Lugol, J.C.; A One Nanosecond Resolution Time–To–Digital Converter; IEEE Transactions On Nuclear Science, vol. NS–30, No. 1, Feb. 1983;pp. 297–300.

* cited by examiner

*Primary Examiner*—Constantine Hannaher
*Assistant Examiner*—Otilia Gabor
(74) *Attorney, Agent, or Firm*—Quarles & Brady LLP; Carl Horton

(57) ABSTRACT

A timing circuit for implementation in a medical imaging system such as a PET scanner, and a method of ascribing times to events in such systems, is disclosed. In one embodiment, the timing circuit includes a quadrature clock, four counter elements, four status circuits, and four output registers. The clock provides four differently-phased clock signals at a single frequency, and the four counter elements respectively receive the clock signals and provide count signals. The four status circuits all receive an event detection signal and further receive the respective clock signals, and in response provide four status signals indicative of whether the event detection signal has experienced a status change. The four output registers receive the respective clock, status and count signals, and in response provide four output signals that are collectively indicative of a time at which the event detection signal experiences the status change.

24 Claims, 8 Drawing Sheets

SYSTEM AND METHOD FOR ASCRIBING TIMES TO EVENTS IN A MEDICAL IMAGING SYSTEM

BACKGROUND OF THE INVENTION

The field of the invention is positron emission tomography (PET) scanners and other similar medical imaging systems, and particularly the event locator circuits or other circuits of PET scanners that are employed to determine the exact times at which photons are detected during PET scans.

Positrons are positively charged electrons which are emitted by radionuclides that have been prepared using a cyclotron or other device. These are employed as radioactive tracers called "radiopharmaceuticals" by incorporating them into substances, such as glucose or carbon dioxide. The radiopharmaceuticals are injected in the patient and become involved in such processes as blood flow, fatty acid, glucose metabolism, and protein synthesis. As the radionuclides decay, they emit positrons. The positrons travel a very short distance before they encounter an electron, and when this occurs, they are annihilated and converted into two photons, or gamma rays. This annihilation is characterized by two features which are pertinent to PET scanners—each gamma ray has an energy of 511 keV and the two gamma rays are directed in nearly opposite directions. An image is created by determining the number of such annihilations at each location within the field of view.

A typical PET scanner is cylindrical and includes a detector ring assembly composed of rings of detectors which encircle the patient and which convert the energy of each 511 keV photon into a flash of light that is sensed by a photomultiplier tube (PMT). Coincidence detection circuits connect to the detectors and record only those photons which are detected simultaneously by detectors located on opposite sides of the patient. The number of such simultaneous events (coincidence events) indicates the number of positron annihilations that occurred along a line joining the two opposing detectors. During an acquisition, coincidence events are recorded to indicate the number of annihilations along lines joining pairs of detectors in the detector ring. These numbers are employed to reconstruct an image using well-known computed tomography techniques.

In order to accurately determine coincidence events and thereby obtain useful information for producing images, PET scanners require timing circuits that accurately identify and log the exact times at which photons are received at the detectors of the scanners. These circuits, which are often referred to as event locator circuits, typically include digital counters that count time periods based upon a digital clock, and digital counter latches that receive both the count signals from the counters and impulse signals from the detectors of the PET scanner whenever photons are detected. Based upon the count signals, the counter latches effectively time-stamp the impulse signals with times indicative of when the impulse signals are received, and output this information for use by the PET scanner in determining coincidence events.

As shown in FIG. 1 (Prior Art), a timing circuit 10 for use in a conventional event locator circuit of a PET scanner includes a delay-line based counter 12 and an asynchronous counter latch 36. The delay-line based counter 12 operates by providing a clock signal 14 from a clock 16 to a binary counter 18 and then to a series of analog delay lines 20, 22 and 24. The binary counter 18, which is shown to be a 5-bit counter, counts the clock pulses from the clock 16 and outputs a 5-bit binary count signal 28. A lowest bit 26 of the binary count signal 28 alternates at the frequency of the clock signal 14, which in FIG. 1 is shown to be a 40 MHz clock having a period of 25 nsec. The binary counter 18 is chosen to be a 5-bit counter in order to allow different times to be distinguished within up to 32 cycles of the clock signal 14.

In order to measure time gradations at an even higher frequency than that of the clock signal 14, the lowest bit 26 of the binary count signal 18 is additionally provided successively to the series of analog delay lines 20–24, which in turn respectively output count signals 30, 32 and 34. The count signals 30, 32 and 34 each take on the same values as the lowest bit 26 of the binary count signal 28, except insofar as each respective count signal takes on the value of the lowest bit only after the passage of respective time delays. In the embodiment shown, in which there are three analog delay lines 20–24, each delay line delays transmission of the lowest bit 26 of the binary count signal 28 by one quarter of the period of the clock, or about 2.5 nsec. Together with the lowest bit 26 of the binary count signal 28, the count signals 30–34 output by the three analog delay lines 20–24 act as a four-bit Johnson-type counter in which the allowable states of the lowest bit of the binary count signal and the three count signals 30–34 are limited to 1000, 1100, 1110, 1111, 0111, 0011, 0001 and 0000. Therefore, by virtue of the analog delay lines 20–24, three additional state changes occur in between each change in the lowest bit 26, such that time intervals are measured at four times the clock frequency, or 100 MHz. The binary count signal 28, together with the other count signals 30–34, form an overall 8-bit count signal 54.

The asynchronous counter latch 36 includes four output registers 38, 40, 42 and 44 that respectively receive the binary count signal 28 and the three additional count signals 30–34 from the binary counter 18 and the analog delay lines 20–24. In particular, the first output register 38 is a 5-bit register capable of storing all 5 bits of the binary count signal 28, while the other output registers 40–44 are single-bit registers capable of storing the individual bits of information of the respective single-bit count signals 30–34. The four output registers 38–44, which are typically D-type flip-flops, further receive and are clocked by an event detection signal 39 that is typically a digital signal provided from one of the acquisition circuits of the PET scanner. The event detection signal 39 typically switches temporarily from a low-level to a high-level whenever photons are received at one or more detectors associated with the particular acquisition circuit. Whenever the output registers 38–44 are clocked by a rising edge of the event detection signal 39, the current values of the binary count signal 28 and the counts signals 30–34 are stored in the respective registers and also output by the registers as respective output signals 45, 46, 47, and 48. Together, the output signals 45–48 form an overall 8-bit output signal 49 that represents the times at which the event detection signal 39 switches and thus the times at which photons are received at the associated detectors of the PET scanner.

Referring additionally to FIG. 2 (Prior Art), a timing diagram 50 shows exemplary operation of the timing circuit 10 of FIG. 1. In particular, the clock signal 14 is shown to vary at a particular frequency, and this is the frequency at which the lowest bit 26 of the 5-bit binary count signal 28 is shown to vary. Additionally, the values of the respective count signals 30, 32 and 34 are shown to follow that of the lowest bit 26 of the binary count signal 28 except insofar as each successive count signal is delayed with respect to the lowest bit by successive 90 degree phase intervals due to the analog delay lines 20, 22 and 24. For example, during a period 52 of the clock signal 14 in which the binary count signal 28 has a value of 00001, the count signal 30 only takes on a high-level value (e.g., a value of 1) one-quarter of the period of the clock signal 14 after the time at which the lowest bit 26 has already taken on a value of 1. Given such operation of the delay-line based counter 12, the overall 8-bit count signal 54 based upon the binary count signal 28 and the count signals 30–34 is determined.

With this progression of the overall 8-bit count signal 54 and the operation of the asynchronous counter latch 36 as explained above, a rising edge in the event detection signal 39 at a time 66 as shown in FIG. 2 should produce the 8-bit output signal 49 also shown in FIG. 2. This is because, when the event detection signal 39 switches from a low-level to a high-level at the time 66, each of the registers 38–44 are clocked and consequently the output signals 45–48 take on the values of the binary count signal 28 and the other count signals 30–34 that currently exist at that time, namely, 00011111.

Although the timing circuit of FIG. 1 has worked well in many PET scanners, the timing circuit may no longer be effective in future PET scanners that require greater timing resolutions (e.g., timing resolutions of better than 1.5 nsec), for several reasons. To begin, analog delay lines have poor temperature and aging characteristics that can lead to inaccuracies in the time delays provided by the delay lines and consequently inaccuracies in the times ascribed to detected events. In higher-resolution machines, the negative impact of such inaccuracies becomes pronounced. Additionally, analog delay lines require physically large packaging schemes and large amounts of circuit board area (often in the range of 100 sq/mm), and also dissipate relatively large amounts of power relative to integrated circuits. As a result, use of the analog delay lines tends to complicate the design and manufacture of event locator circuits, and consequently increase the manufacturing and design costs for those circuits.

A further problem that arises from the use of timing circuits such as that shown in FIG. 1 relates to metastability of the output registers 38–44. More specifically, because the count signals 28–34 are asynchronously clocked into the output registers 38–44 by the event detection signal 39, the proper count values may not be stored and output by the registers. For example, as shown in FIG. 3 (Prior Art), prior to the switching of each count signal 28, 30, 32 and 34, there is a period of time 58, 60, 62 and 64, respectively, at which the respective output registers 38, 40, 42 and 44 are metastable. Consequently, if the event detection signal 39 happens to switch from a low level to a high level at a time 68 during one of the metastable periods 58 corresponding to the first (5-bit) output register 38, the 5-bit count value that will be stored by the register and provided as the output signal 45 is unpredictable and can take on any one of eight values 00000, 00001, 00010, 00011, 00100, 00101, 00110, and 00111. As a result, the 8-bit output signal 49 can take on eight different values 70 as shown. This is in contrast to FIG. 1, where the rising edge of the event detection signal 39 occurs at the time 66 that does not coincide with any of the metastable periods 58–64, and consequently the 8-bit output signal 49 takes on the appropriate count value.

Further referring to FIG. 3, in the example that is shown, only three of the bits 72 of the 8-bit output signal 49 can take on inappropriate values due to the effects of metastability. This is because the rising edge of the event detection signal 39 occurs during the metastable period 58 just prior to switching of the binary count signal 28 from a count of 00011 to a count of 00100, in which the lowest three bits of the binary count signal are switched. Others of the metastable periods 58 precede changes in the binary count signal 28 that involve different bits than the three lowest bits, and/or involve a different number of bits. Consequently, rising edges in the event detection signal 39 that occur during these other metastable periods 58 can cause different errors in the 8-bit output signal 49.

Further, if the rising edge of the event detection signal 39 occurs during any of the metastable periods 60, 62 and 64, only a single bit error can be produced within the 8-bit output signal 49, since each of these metastable periods precedes a single-bit change in one of the count signals 30–34. Although involving only a single bit, such an error often is unacceptable with respect to the count signals 30–34 because it can produce a value of the overall 8-bit output signal 49 that is undefined (e.g., 000101 01 would be unacceptable since the lowest three bits are not ever supposed to take on the value 101).

These effects of metastability in timing circuits, although tolerable for many conventional PET scanners, become more problematic as timing resolutions are increased. This is particularly the case insofar as the lengths of the metastable periods for registers are not decreasing as rapidly as the frequency of operation of the clocks of the timing circuits (and overall rapidity of operation of the PET scanners) is increasing.

It would therefore be advantageous if a system and method for ascribing times to events that are detected in medical imaging systems such as PET scanners were developed that could measure and count small time gradations (e.g., time gradations of less than 1.5 nsec) by way of a technology that was more accurate, less consumptive of power, physically smaller, and less costly than analog delay lines. It would further be advantageous if such a system and method for ascribing times to detected events could limit the errors introduced as a result of metastability. In particular, it would be advantageous if, in such a system and method, ascribed times differed from the correct times by no more than one of the smallest-level time gradations measured by the system. It would additionally be advantageous if, in the case where such a system and method employed a counting system in which the count did not pass through all possible numeric states, the system and method would avoid the introduction of errors in which the count would take on undefined numeric states.

SUMMARY OF INVENTION

It has been discovered that a timing circuit of a medical imaging system such as a PET scanner can employ a quadrature clock using a phase locked loop circuit and two inverters in order to effectively provide a clock signal that is four times that of the actual frequency of operation of the phase locked loop circuit. The phase locked loop circuit specifically provides a first pair of clock signals that share the same frequency but are shifted in phase 90 degrees relative to one another. An additional pair of clock signals that respectively are inverted versions of the first two clock signals are produced by way of the two inverters. Thus, four clock signals are produced that share the same frequency but are shifted in phase 90 degrees relative to one another, and so effectively a clock of four times the actual clock frequency is generated, without use of analog delay lines.

Additionally, it has been discovered that it is possible to mitigate the generation of errors in the times ascribed to detected events due to the metastability of output registers of the timing circuits, by employing a status detection circuit to process an event detection signal prior to providing the information of the event detection signal to the output registers, and then synchronously (with computer signals) providing the information to the output registers. In one embodiment that operates in conjunction with the quadrature clock discussed above, the status detection circuit is a quadrature edge detection circuit with four shift registers that are respectively, separately clocked by the four clock signals of the quadrature clock. Additional respective sets of digital circuit elements coupled to the respective shift registers respectively provide edge detection signals to the respective output registers that allow updating in the overall output count only when a rising edge in the event detection signal has occurred. Because each shift register is clocked by its respective clock signal at different times than are the other shift registers, any given rising edge of the event detection signal can only occur during the metastable period of one of the shift registers. Therefore, because each shift register controls the output activity of only the respective output register to which it is coupled, the occurrence of a rising edge during a metastable period of one of the shift registers will only introduce, at most, errors in the portion of the overall output signal that is produced by the output register corresponding to that shift register.

In particular, the present invention relates to a timing circuit for use in a medical imaging system. The timing circuit includes a clock, a counter, a status detection circuit, and an output circuit. The clock has a primary frequency of operation, and the clock provides at least a first clock signal that varies at the primary frequency. The counter includes first and second counter elements coupled to the clock. The first counter element receives the first clock signal and in response provides a first count signal that varies at the primary frequency. The second counter element receives a second clock signal, and in response provides a second count signal. The status detection circuit includes first and second status circuits coupled to the clock. The first status circuit receives the first clock signal and an event detection signal and in response provides a first status signal indicative of whether the event detection signal has experienced a first status change. The second status circuit receives the second clock signal and the event detection signal and in response provides a second status signal indicative of whether the event detection signal has experienced the first status change. The output circuit includes first and second registers coupled to the clock and respectively coupled to the first and second counters and to the first and second status circuits. The first and second registers respectively receive the first and second clock signals, the first and second count signals, and the first and second status signals, respectively, and in response respectively provide first and second output signals that collectively form an overall output signal indicative of a time at which the event detection signal experienced the first status change.

The present invention further relates to a PET scanner that includes a plurality of detectors supported by a gantry, a plurality of acquisition circuits coupled to the detectors, and a plurality of event locator circuits. The acquisition circuits provide event detection signals that are related to signals received from detectors indicating that photons have been detected, and the plurality of event locator circuits receive the event detection signals. Each event locator circuit includes a respective quadrature clock and a respective quadrature counter coupled to the respective quadrature clock. Each event locator circuit additionally includes a respective quadrature edge detection circuit coupled to the respective quadrature clock and further coupled to at least one of the acquisition circuits to receive a respective one of the event detection signals. Each event locator circuit further includes a respective quadrature count latch circuit coupled to the respective quadrature clock, the respective quadrature counter and the respective quadrature edge detector. The respective quadrature count latch circuit provides a respective output signal indicative of times at which the respective event detection signal undergoes transitions of a particular type. The respective quadrature edge detection circuit prevents the respective output signal from at least one of attaining values that are undefined and attaining values that are indicative of incorrect times that are more than one clock cycle in error relative to the times at which the respective event detection signal undergoes the transitions.

The present invention further relates to a timing circuit for implementation in a medical imaging device. The timing circuit includes a phase locked loop circuit employed to generate at least two clock signals having the same frequency and each having a different phase relative to one another. The timing circuit additionally includes a means for providing a count signal based upon the at least two clock signals; and a means for associating and outputting a particular count of the count signal with a status change of an event detection signal, where the particular count is indicative of a time at which the status change occurred.

The present invention additionally relates to a method of ascribing times to events in a medical imaging system. The method includes generating a plurality of clock signals at a phase locked loop circuit, where all of the clock signals have the same frequency but have different phases, and providing each clock signal to a respective counter element. The method further includes generating at each counter element a respective count signal, where the count signals together represent successive time increments, and where the time increments are smaller than a period of the clock signals. The method additionally includes providing an event detection signal and the plurality of clock signals to a plurality of status circuits, where each clock signal is provided to a respective status circuit. The method also includes determining at each status circuit, at times at which the respective clock signals change in their states, whether the event detection signal has undergone a particular status change. The method further includes generating at each status circuit a respective status signal, where each respective status signal attains a particular level whenever the respective status circuit determines that the event detection signal has undergone the particular status change. The method additionally includes receiving at respective storage elements the respective clock signals, status signals and count signals. The method further includes storing values of the respective count signals in the respective storage elements at times when respective clock signals change in their states and when the respective status signals have attained the particular level, and outputting the stored values, as an overall output signal that indicates times at which the event detection signal has undergone the particular status change.

DETAILED DESCRIPTION

Figure 4:
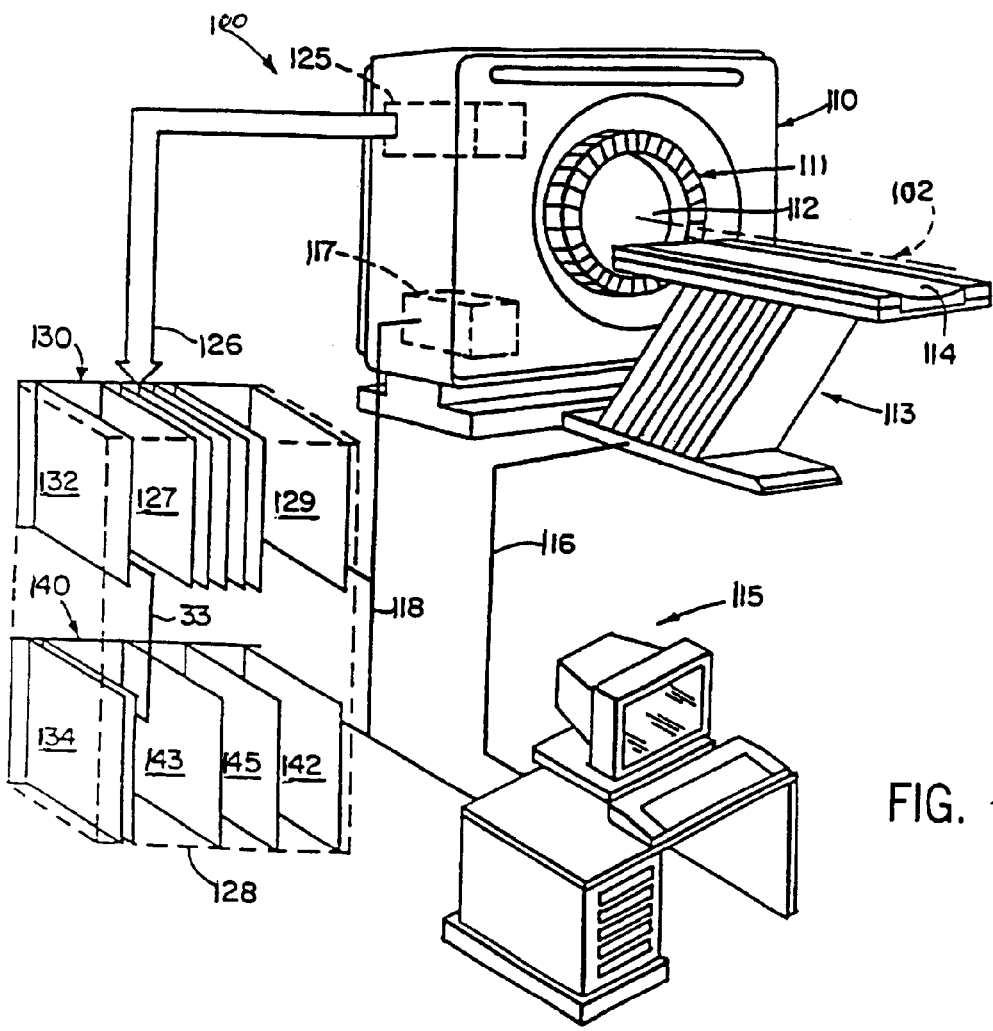
FIG. 4 is a pictorial view with parts cut away of an exemplary medical imaging system, shown to be a PET scanner, that is capable of employing the present invention.

Referring particularly to FIG. 4, a PET scanner 100 is shown. The PET scanner 100 is intended to be representative of a variety of different types of medical imaging systems in which accurate timing circuitry is employed including, but not limited to, Nuclear Magnetic Resonance (NMR) imaging systems and Computed Tomography (CT) imaging systems. The PET scanner 100 includes a gantry 110 which supports a detector ring assembly 111 about a central opening, or bore 112. The detector ring assembly 111 is circular in shape, and is made up of multiple detector rings (not shown) that are spaced along a central axis 102 to form a cylindrical detector ring assembly. A patient table 113 is positioned in front of the gantry 110 and is aligned with the central axis 102 of the detector ring assembly 111. A patient table controller (not shown) moves the table bed 114 into the bore 112 in response to commands received from an operator work station 115 through a serial communications link 116. A gantry controller 117 is mounted within the gantry 110 and is responsive to commands received from the operator work station 115 through a local area network 118 to operate the gantry.

Figure 6:
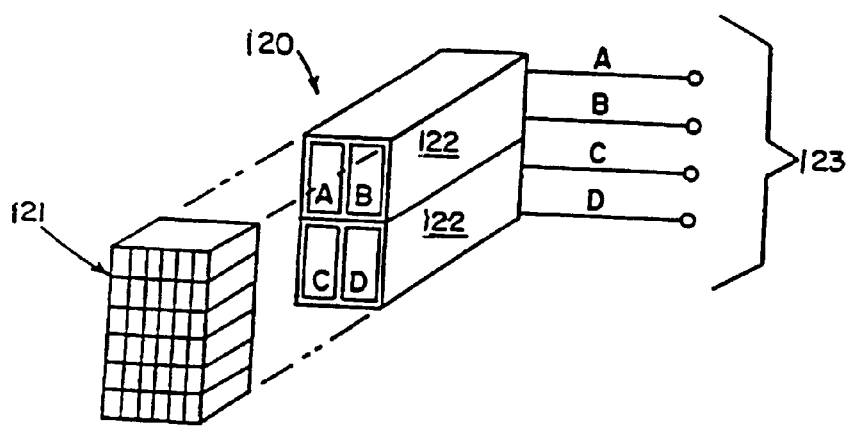
FIG. 6 is a pictorial view of a detector which forms part of the PET scanner of FIG. 4.
Figure 5:
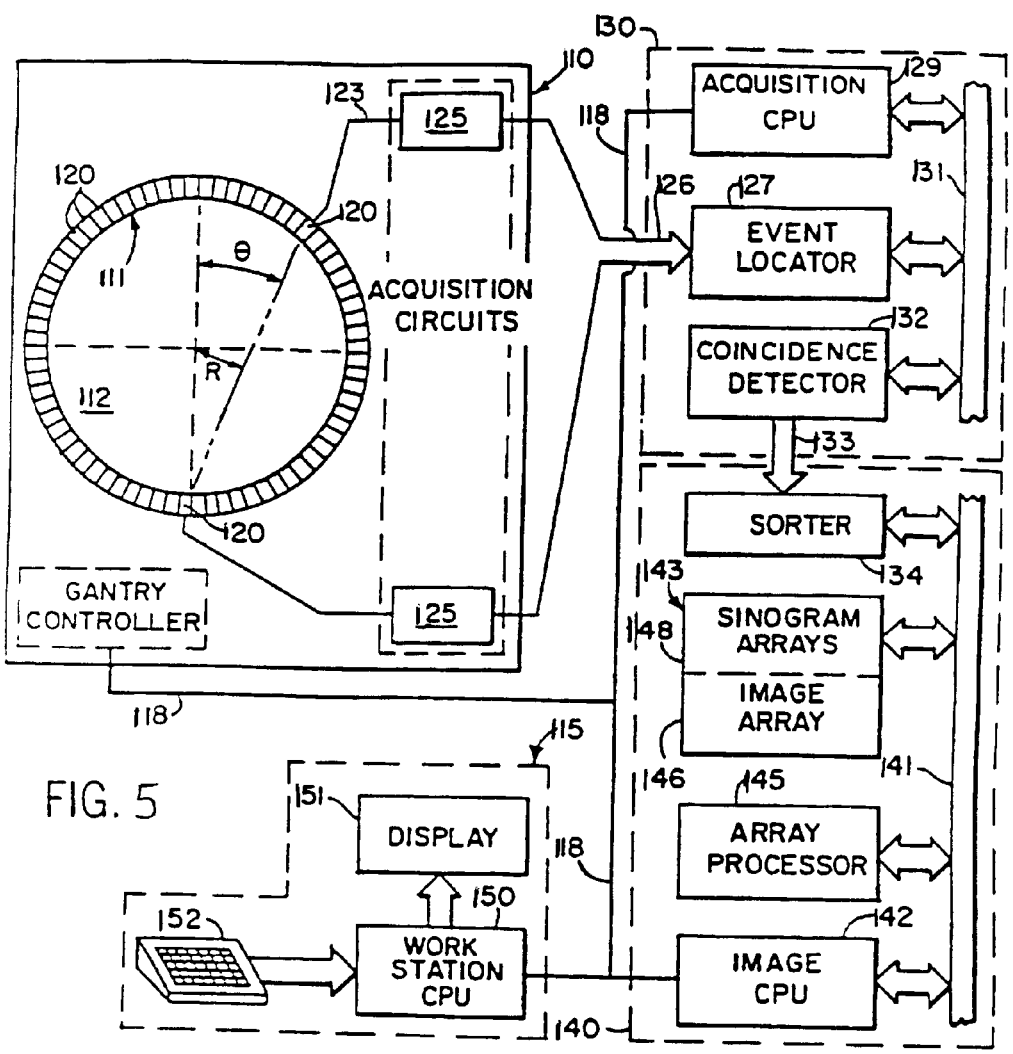
FIG. 5 is a schematic diagram of the PET scanner of FIG. 4.

As shown in FIGS. 4–6, each detector ring of the detector ring assembly 111 is comprised of detectors 120. Each detector 120 includes a scintillator or BGO crystal 121. Each BGO crystal 121 is disposed in front of a photomultiplier tube 122 (abbreviated PMT). More than one BGO crystal 121 may be disposed in front of a given PMT 122. For example, in one embodiment (shown in FIG. 6) a matrix of 36 BGO crystals 121 is disposed in front of four PMTs 122, such that 9 BGO crystals are disposed in front of each of the PMTs. All of the PMTs 122 produce analog signals on line 123 when a scintillation event occurs at one of the respective 9 BGO crystals 121 that are disposed in front of the PMTs (i.e., when a photon is received by one of the BGO crystals 121). A set of acquisition circuits 125 is mounted within the gantry 110 to receive these signals and produce digital signals indicating the event coordinates (x,y) and the total energy. These are sent through a cable 126 to an event locator circuit 127 housed in a separate cabinet 128. Each acquisition circuit 125 also produces an event detection signal that includes event detection pulses (EDPs) when scintillation events took place.

Referring particularly to FIGS. 4 and 5, the event locator circuits 127 form part of a data acquisition processor 130 which periodically samples the signals produced by the acquisition circuits 125. The processor 130 has an acquisition CPU 129 which controls communications on the local area network 118 and a backplane bus 131. The event locator circuits 127 assemble the information regarding each valid event into a set of digital numbers that indicate precisely when the event took place and the position of the detector 120/crystal 121 which detected the event. This event data packet is conveyed to a coincidence detector 132 which is also part of the data acquisition processor 130.

The coincidence detector 132 accepts the event data packets from the event locators 127 and determines if any two of them are in coincidence. Coincidence is determined by a number of factors. First, the time markers in each event data packet must be within a certain time amount of each other, and second, the locations indicated by the two event data packets must lie on a straight line which passes through the field of view (FOV) in the scanner bore 12. Events which cannot be paired are discarded, but coincident event pairs are located and recorded as a coincidence data packet that is conveyed through a serial link 133 to a sorter 134. For a detailed description of the coincidence detector 132, reference is made to U.S. Pat. No. 5,241,181 entitled "Coincidence Detector For A PET Scanner" which is incorporated herein by reference.

The sorter 134 forms part of an image reconstruction processor 140. The sorter 134 counts all events occurring along each projection ray and organizes them into a two dimensional sinogram array 148 which is stored in a memory module 143. The image reconstruction processor 140 also includes an image CPU 142 that controls a backplane bus 141 and links it to the local area network 118. An array processor 145 also connects to the backplane bus 141 and it reconstructs images from the sinogram arrays 148. The resulting image array 146 is stored in memory module 143 and is output by the image CPU 142 to the operator work station 115. For a detailed description of the sorter 134, reference is made to U.S. Pat. No. 5,272,343 entitled "Sorter For Coincidence timing Calibration In A PET Scanner" which is incorporated herein by reference.

The operator work station 115 includes a CPU 150, a CRT display 151 and a keyboard 152. The CPU 150 connects to the local area network 118 and it scans the keyboard 152 for input information. Through the keyboard 152 and associated control panel switches, the operator can control the calibration of the PET scanner, its configuration, and the positioning of the patient table for a scan. Similarly, the operator can control the display of the resulting image on the CRT display 151 and perform image enhancement functions using programs executed by the work station CPU 150.

Figure 7:
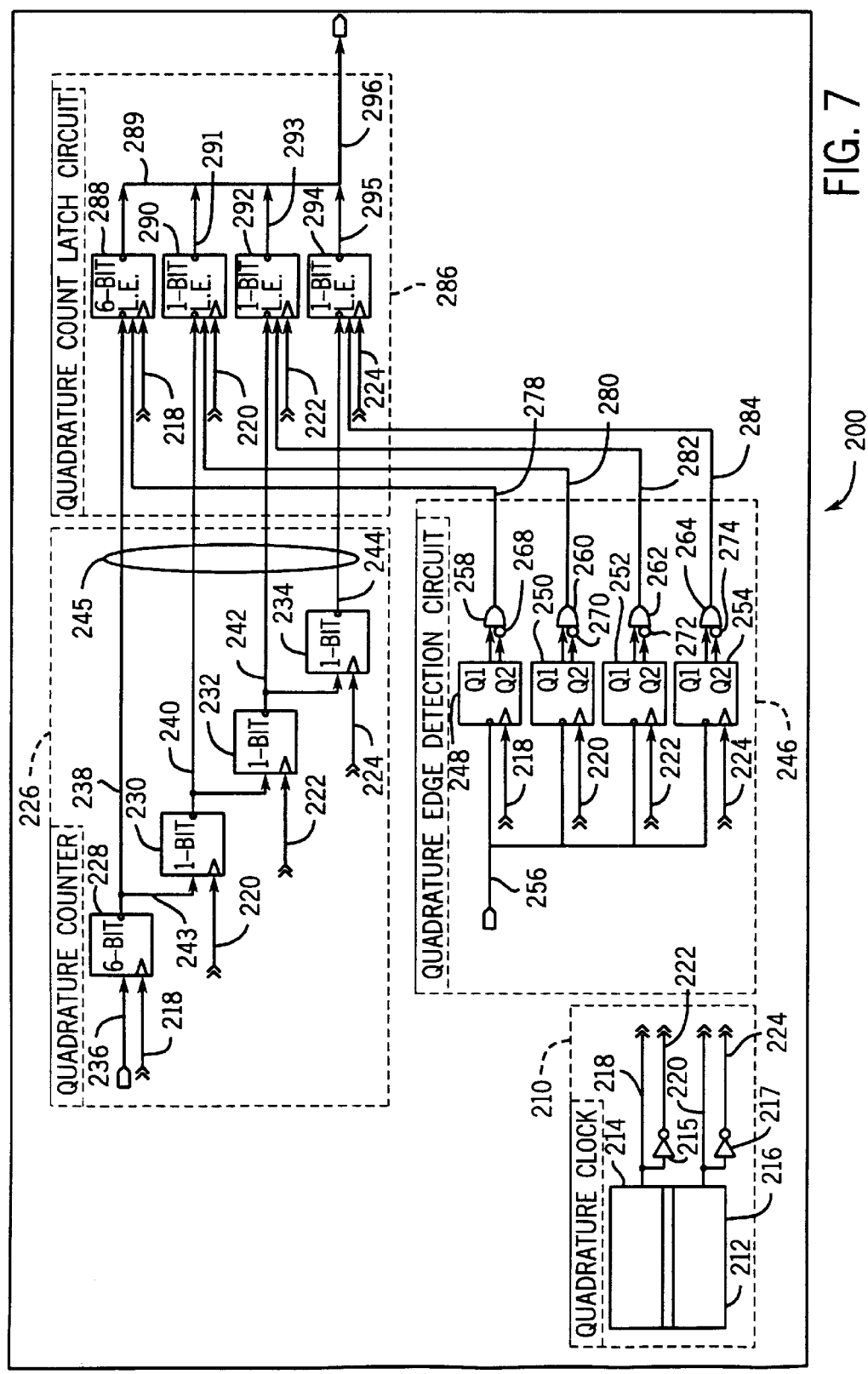
FIG. 7 is a schematic diagram of a new timing circuit that can be employed in a medical imaging system such as the PET scanner of FIG. 4, in accordance with one embodiment of the present invention.

Turning to FIG. 7, an exemplary embodiment of a new timing circuit 200 for ascribing times to detected events in a PET scanner such as the PET scanner 100 discussed above or other medical imaging systems is shown to include a quadrature clock 210, and quadrature counter 226, a quadrature edge detection circuit 246, and a quadrature count latch circuit 286. Each of these circuits 210, 226, 246 and 286 can be implemented on a field programmable gate array microcircuit or other electronic device as part of a respective event location circuit 127. Typically, several of the timing circuits 200 are implemented on a single field programmable gate array.

The quadrature clock 210 includes a phase locked loop circuit 212 that is capable of providing clock signals at a frequency of 192 MHz, such that the period of the clock is 5.208 nsec. In alternate embodiments, the clock 210 can provide clock signals that vary at other frequencies. Further as shown, the phase locked loop circuit 212 includes a first phase locked loop macro 214 and a second phase locked loop macro 216 that respectively produce first and second clock signals 218, 220 that respectively share the same frequency but differ from one another by 90 degrees in phase. Additionally, the quadrature clock 210 includes a first inverter 215 and second inverter 217 that respectively produce a third clock signal 222 and a fourth clock signal 224, which are respectively 180 degrees out of phase with the first and second clock signals 218, 220. Thus, the quadrature clock 210 outputs first, second, third, and fourth clock signals 218–224 that share the same frequency of operation but are successively shifted 90 degrees in phase relative to one another.

The four clock signals 218–224 are in turn provided to the quadrature counter 226. As shown, the quadrature counter 226 includes a 6-bit binary counter 228, and three single-bit counters 230, 232, and 234. The 6-bit counter 228 can be a binary counter of any type known in the art, while the single-bit counters 230–234 are each shown to be single-bit D-flip-flops. Specifically, the first clock signal 218 is provided as the clock input to the binary counter 228 along with a reset input, which allows the output of the binary counter to be reset. The binary counter 228 in turn outputs a 6-bit binary count signal 238, which has a lowest bit 243 that varies at the frequency of the clock signal 218.

The lowest bit 243 of the binary count signal 238 is provided as the D input of the counter 230, which receives also the second clock signal 220 as its clock input. In response, the counter 230 outputs a single-bit count signal 240, which in turn is provided to the next counter 232 as its D input. The counter 232 additionally receives the third clock signal 222 as its clock input and in response provides an additional single-bit count signal 242. The count signal 242 in turn is provided as the D input of the last counter 234, which receives the fourth clock signal 224 as its clock input and in response provides a final count signal 234. Because the clock signals 218–224 are successively shifted 90 degrees in phase relative to one another, the quadrature counter 226 provides an overall 9-bit count signal 245 that is essentially the same as the overall 8-bit count signal 54 produced by the delay-line based counter 12 discussed above (except insofar as the binary count signal 238 includes six bits rather than five bits as in the case of the 5-bit binary counter 18).

Figure 8:
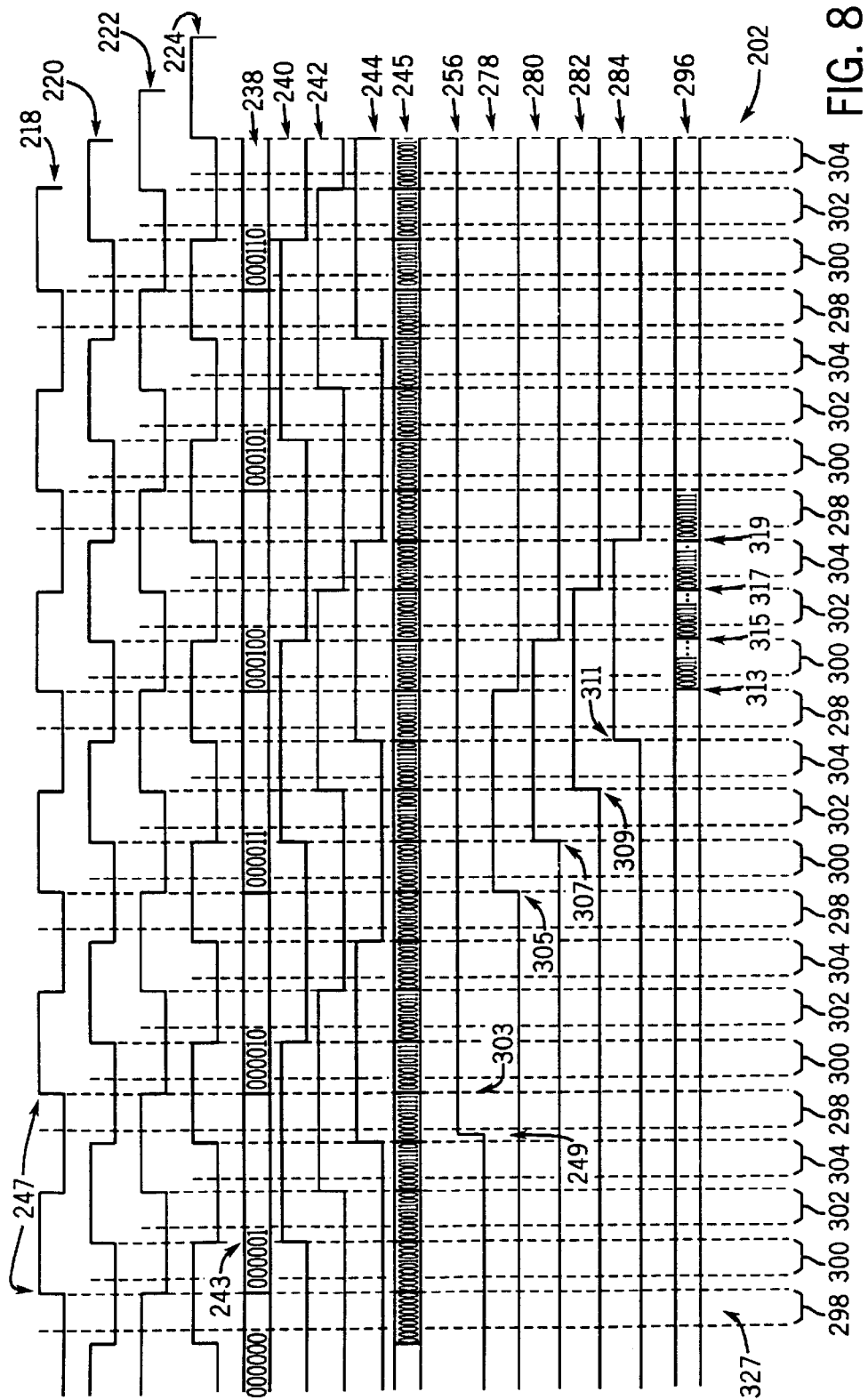
FIG. 8 is a timing diagram showing operation of the timing circuit of FIG. 7 in which metastability of elements of the timing circuit does not affect the output-signals of the timing circuits.

Turning to FIG. 8, a timing diagram 202 shows exemplary operation of the quadrature clock 210 and quadrature counter 226 of the timing circuit 200. In particular, FIG. 8 shows the first, second, third and fourth clock signals 218–224 to be successively shifted 90 degrees in phase relative to one another. Further, the 6-bit binary count signal 238 is shown to include the lowest bit 243 that varies at the same frequency as the clock signals 218–224 and in particular changes in value with rising edges 247 of the first clock signal 218. Further, the count signals 240, 242 and 244 are also shown to switch on and off as the same frequency at the lowest bit 243 switches on and off, except insofar as each respective count signal 240–244 is delayed 90 degrees in phase relative to the previous respective count signal 238–242, respectively. Thus, the successive 90 degree shifts in phase of the clock signals 218–224 gives rise to the same overall count signal 245 as generated by the delay-based counter 12 (that is, the same as the overall count 54), except insofar as it is a 9-bit count signal rather than a 8-bit count signal. That is, the lowest bit 243 of the binary count signal 238 and the count signals 240–244 output by the counters 230–234 together act as a four-bit Johnson type counter in which the allowable states of the lowest bit of the binary count signal and the three count signals 238–244 are limited to 1000, 1100, 1110, 1111, 0110, 0011, 0001, 0000.

Figure 1:
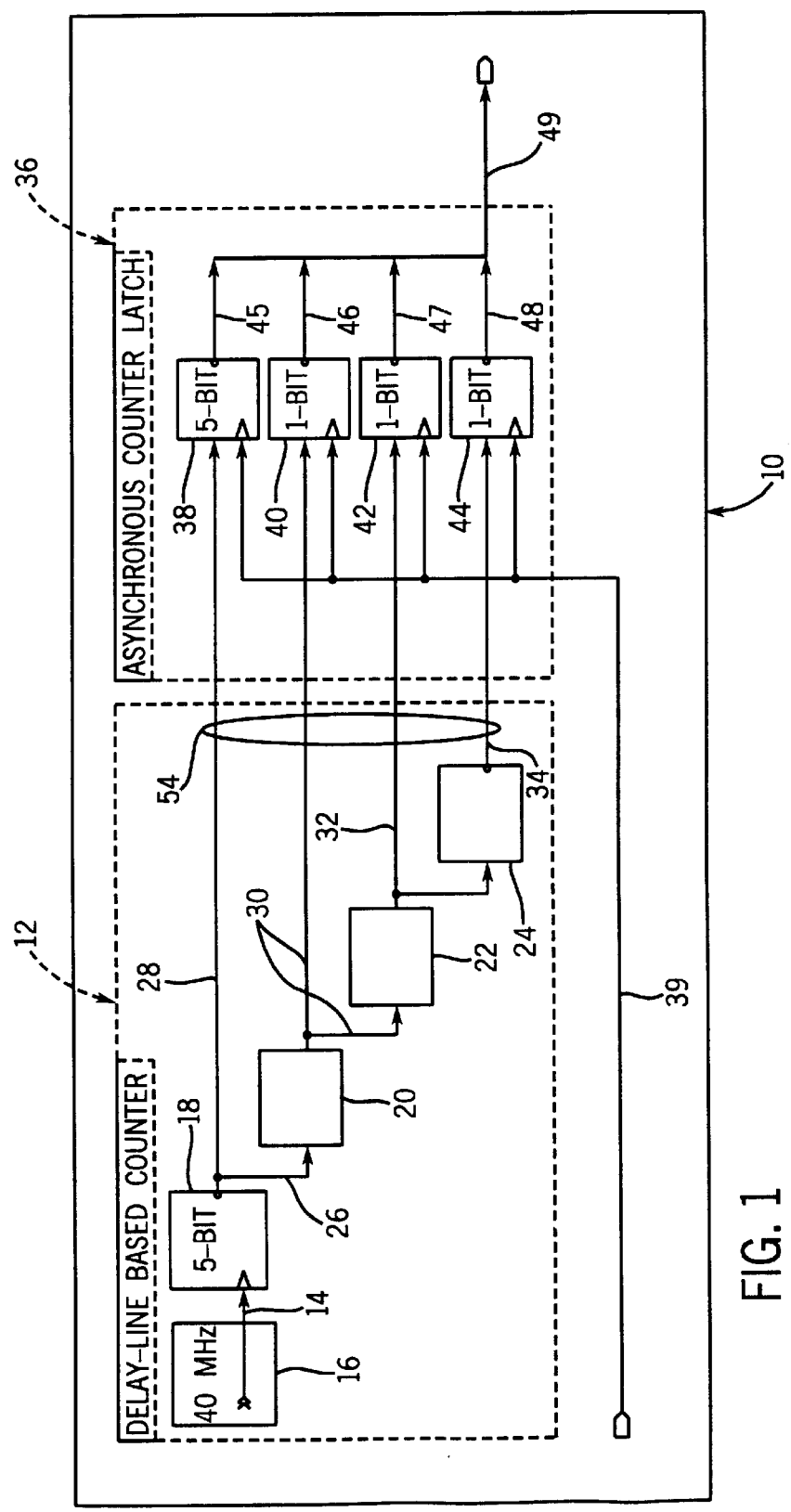
FIG. 1 (Prior Art) is a schematic diagram of a conventional timing circuit employed in a medical imaging system such as a PET scanner.
Figure 2:
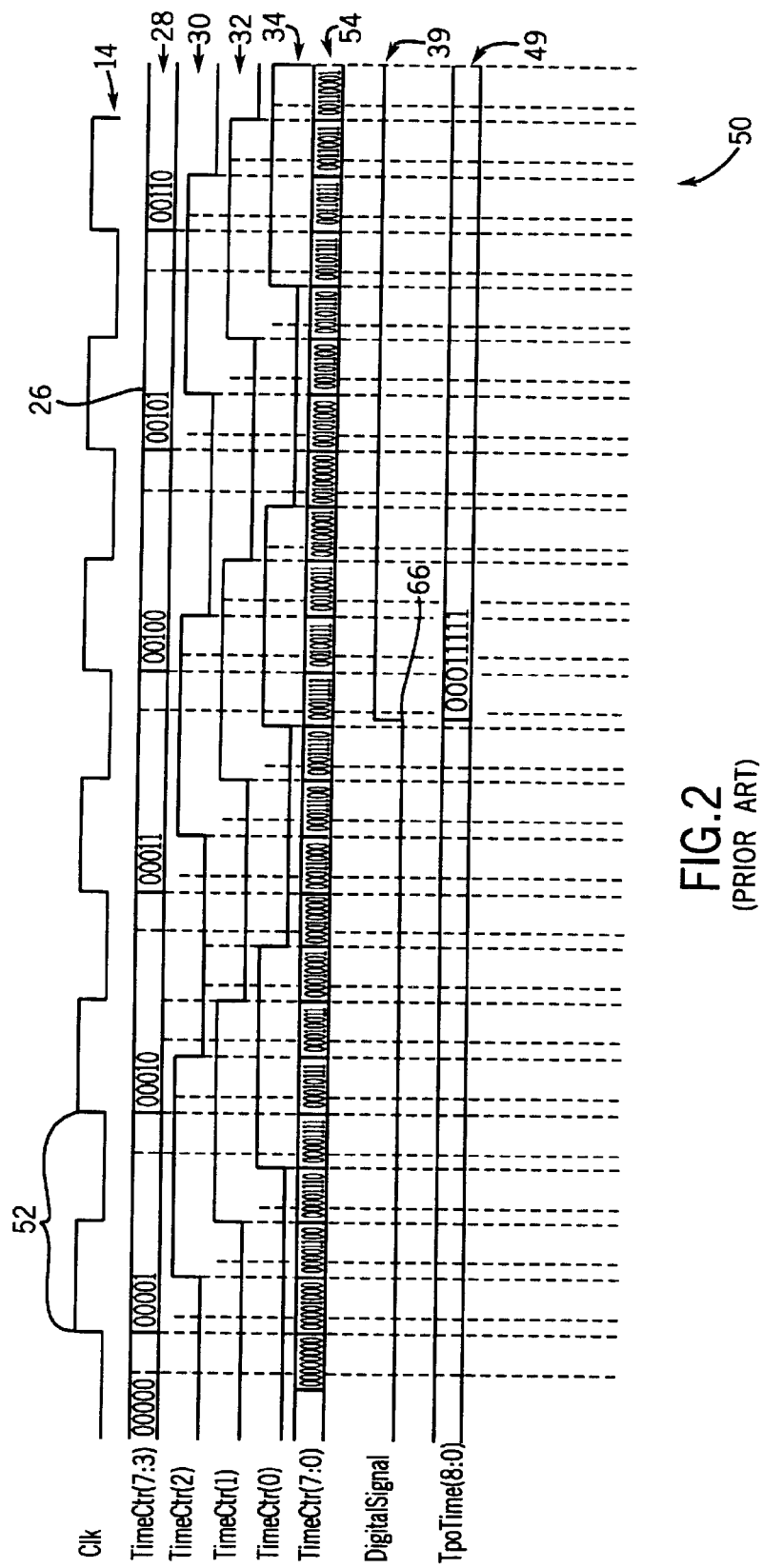
FIG. 2 (Prior Art) is a timing diagram showing proper operation of the timing circuit of FIG. 1.
Figure 3:
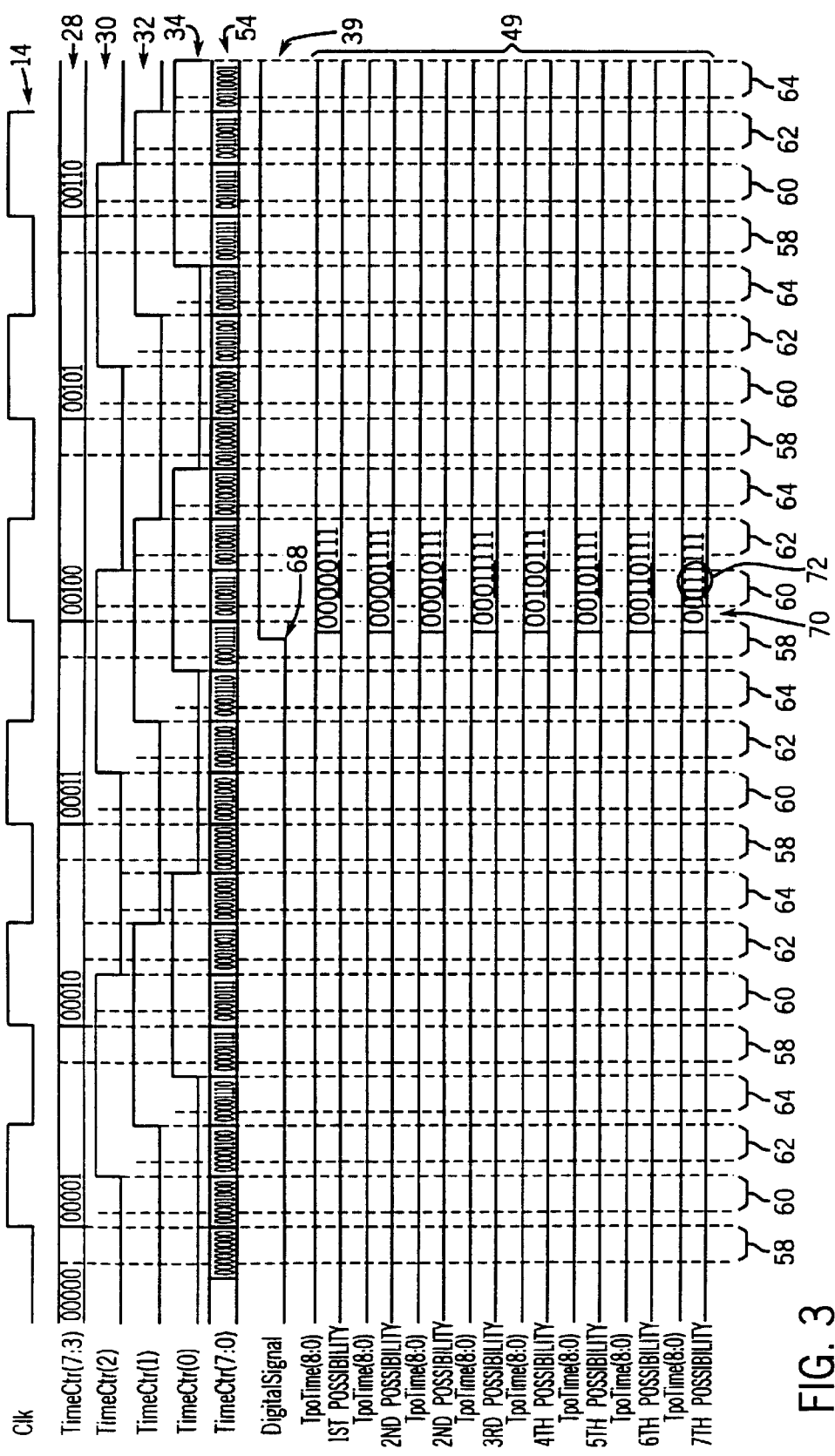
FIG. 3 (Prior Art) is a timing diagram showing operation of the timing circuit of FIG. 1 in which metastability causes excessive error to be introduced into a time being ascribed to a detected event.

Although the quadrature clock 210 and the quadrature counter 226 provide essentially the same count signal 245 as that of the delay-line based counter 12, the quadrature clock and counter also offer significant benefits relative to the counter 12. Because the quadrature clock 210 provides four clock signals 218–224 that are successively shifted 90 degrees in phase relative to one another, analog delay lines are not necessary for providing delayed counts as in the delay-line based counter 12. Therefore, especially insofar as multiple quadrature clocks 210 and quadrature counters 226 of multiple event locator circuits 127 can be implemented on a single field programmable gate array chip (not shown), much less physical space is required for clock/counter circuitry than is required by the conventional circuitry of FIG. 1. Additionally, other disadvantages associated with the analog delay lines 20–24, including the high levels of heat dissipated by the analog delay lines and the timing inaccuracies that can be introduced by the analog delay lines, are alleviated through the use of the quadrature clock 210 and counter 226. Further, the use of the quadrature clock 210 and counter 226 is less costly than the use of the analog delay lines 230–234 insofar as it is not necessary to incur the high design and manufacturing costs associated with accounting for the larger space and heat dissipation requirements of the analog delay lines.

Further referring to FIG. 7, the quadrature edge detection circuit 246 includes four shift registers 248, 250, 252 and 254, respectively, that are respectively coupled to and clocked by the four clock signals 218, 220, 222 and 224. The shift registers 248–254 can be conventional shift registers such as D flip-flop type shift registers in which an output of the shift register (or stored value of the shift register) is set equal to an input value upon receiving a clock pulse, e.g., a rising edge of a clock signal provided to the shift register. In the embodiment shown, each of the shift registers 248–254 are four-bit shift registers having four outputs Q0, Q1, Q2 and Q3 (Q0 and Q3 not being shown), and the D input of each of the shift registers 248–254 is coupled to an event detection signal 256 provided from one of the acquisition circuits 125 of the PET scanner 100. In the present embodiment, the event detection signal 256 is a digital signal that changes from a low level to high level (e.g., experiences a rising edge) whenever an event is detected, although in alternate embodiments other types of signals can be provided as the event detection signal. The quadrature edge detection circuit 246 additionally includes four AND gates 258, 260, 262 and 264 that are respectively coupled to the four shift registers 248–254. In the embodiment shown, a first input of each of the AND gates 258–264 is coupled directly to the Q1 output its respective shift register 248–254, while a second input of each of the AND gates is indirectly coupled to the Q2 output of its respective shift register by way of a respective inverter 268, 270, 272 and 274. As their output signals, the AND gates 258–264 provide respective edge detection signals 278–284, which are the output signals of the quadrature edge detection circuit 246.

The edge detection signals 278–284 are respectively provided to four additional output registers 288, 290, 292 and 294, respectively, which make up the quadrature count latch circuit 286. Each of the output registers 288–294 in the present embodiment is a D flip-flop type of register, although other types of registers can be used in alternate embodiments. The first output register 288 is a 6-bit register that receives as its clock input the first clock signal 218, and receives as its input signal the 6-bit binary count signal 238. Additionally, the output register 288 receives a latch enable signal that is the first edge detection signal 278. For this reason, the first edge detection signal 278 (as well as the other edge detection signals) can be understood to be a latch signal. The first output register 288 operates by storing the current value of the binary count signal 238 whenever a rising edge of the first clock signal 218 is provided, so long as the value of the first edge detection signal 278 at the time of the rising edge is at a high level. The output register 288 in turn provides as an output signal 289 the 6-bit value that is currently being stored by the register 288.

The remaining output registers 290, 292 and 294 are single-bit registers that are respectively provided with the count signals 240, 242 and 244 as inputs. However, except in terms of the number of bits stored in the registers 290–294, the registers operate similarly to the 6-bit register 288 in that each register is clocked by a respective one of the clock signals 220–224 and further receives a respective one of the edge detection signals 280–284 as a latch enable signal. Each of the single-bit registers 290–294 stores an updated value of the respective count signals 240–244 only at such times as rising edges of the respective clock signals 220–224 occur while the respective edge detection signals 280–284 are at high levels. Additionally, each of the single-bit registers 290–294 produces a respective single-bit output signal 291, 293 and 295, which are combined with the 6-bit output signal 289 to produce an overall 9-bit output signal 296.

Figure 9:
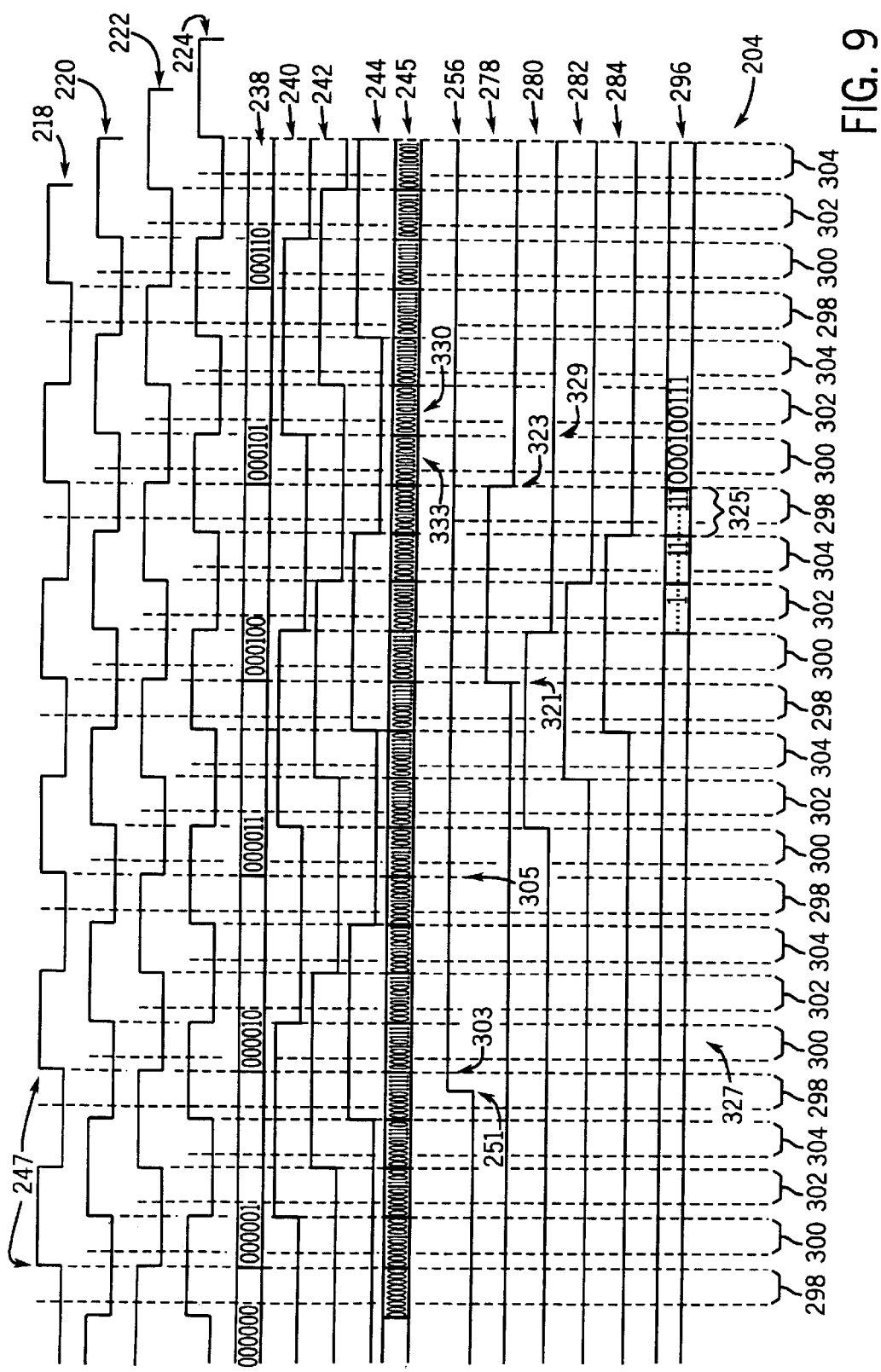
FIG. 9 is a timing diagram showing operation of the timing circuit of FIG. 7 in which metastability of an element of the timing circuit affects the output signals of the timing circuit.

Referring again to FIG. 8 and also FIG. 9, two timing diagrams 202, 204 showing exemplary operation of the timing circuit 200 in generating the overall output signal 296 by way of the quadrature edge detection circuit 246 and the quadrature count latch circuit 286 are provided. As shown in each timing diagram, respective metastable periods 298, 300, 302 and 304 occur in the respective shift registers 248, 250, 252 and 254 of the quadrature edge detection circuit 246 just prior to the rising edges 247 of each respective clock signal 218, 220, 222 and 224. In particular, FIG. 8 shows exemplary operation of the timing circuit 200 in a circumstance where the event detection signal 256 switches from a low level to a high level at a time 249 just prior to one of the metastable periods 298 corresponding to one of the rising edges 247 of the first clock signal 218. In contrast, FIG. 9 shows exemplary operation of the timing circuit 200 in a circumstance where the event detection signal 256 switches from a low level to a high level at a time 251 within one of the metastable periods 298 just prior to the rising edge of the clock signal 218.

Because these rising edges of the event detection signal 256 at times 249, 251 both occur after the previous earliest rising edge of one of the clock signal 218–224 at time 247 and before the same rising edge of the first clock signal 218, ideally the timing circuit 200 would output the same overall 9-bit output signal 296 indicating that the two rising edges of the event detection signal occurred at the same time. However, as shown, the overall output signals 296 do differ between the two different timing diagrams 202, 204, between the overall count value 000011111 and 000100111 because of the effects of metastability. Nevertheless, the design of the timing circuit 200 and particularly the operation of the quadrature edge detection circuit 246 guarantees that the difference between the two different times ascribed to the detected event will not exceed an amount corresponding to the smallest gradation of time measured by the quadrature clock 210, that is, a time period 325 corresponding to 90 degrees of phase of any one of the clock signals 218–224 or 1.302 nsec. That is, even though the metastability of the timing circuit 200 introduces a minor error in the overall output signal 296 shown in FIG. 9 relative to that shown in FIG. 8, the resulting error is limited to at most one count difference between the erroneous signal and the correct signal.

The ability of the timing circuit 200 to limit the amount of error due to metastability is due to the operation of the quadrature edge detection circuit 246 and the quadrature count latch circuit 286, which is specifically shown in FIGS. 8 and 9. Referring to FIG. 8, through the operation of the quadrature edge detection circuit 246, the rising edge of the event detection signal 256 at the time 249 is accepted as an input by the first shift register 248 upon the next occurrence of the rising edge 247 of the first clock signal 218 at a time 303. Because of the operation of the shift register 248, it takes an additional full cycle of the first clock signal 218 for the original input (stored as Q0) to become the value of Q1 of the shift register 248. Once it does so, at a time 305 the values of Q1 and Q2 become 1 and 0 respectively, and so the AND gate 258 causes the first edge detection signal 278 to switch to a high level. The first edge detection signal 278 only remains at the high level for one cycle of the first clock signal 218, since the next rising edge of the clock signal causes the Q1 and Q2 values of the shift register 248 to both become equal to 1, which in turn causes the AND gate 258 to return the edge detection signal 278 to a low value (due to the operation of the inverter 268).

Similarly, in response to the switching of the event detection signal 256 at the time 249, each of the other shift registers 250–254 first output Q1 values of 1 at respective times 307, 309 and 311. As with the first shift register 248, each of these shift registers 250–254 subsequently (one clock cycle later) shift to providing Q1 and Q2 values that are both equal to 1, such that the respective edge detection signals 280–284 only remain at a high level for single cycles of their respective clock signals 220–224. Thus, when the event detection signal 256 experiences a rising edge, it causes each of the edge detection signals 278–284 to attain a high level for exactly one clock cycle, but the respective edge detection signals attain their respective high levels during time periods that are shifted 90 degrees relative to one another.

As discussed, each of the registers 288–294 only accept new updated count values from the count signals 238–244 at such times as the respective edge detection signals 278–284 are higher at a high level, and specifically only upon the receipt of rising edges of the respective clock signals 218–224. Thus, in the example shown in FIG. 8, the 6-bit register 288 accepts and outputs an updated value (000011) of the 6-bit count signal 238 upon the occurrence of a rising edge 247 of the first clock signal 218 at a time 313, since at that time the first edge detection signal 278 is still at a high level (and just about to return to its low level). Similarly, at successive times 315, 317 and 319 at which the next rising edges 247 of the respective clocks 240, 242 and 244 occur and the respective edge detection signals 280, 282 and 284 are still at high levels, updated values of the count signals 240, 242 and 244 are accepted and outputted by the registers 290, 292 and 294. In this case, the updated values of each of the count signals 240–244 are each equal to 1 and so the overall output signal 296 takes on a value of In contrast to FIG. 8, FIG. 9 shows the operation of the quadrature edge detection and count latch circuits 246, 286 when the event detection signal 256 experiences a rising edge at the time 251 during one of the metastable periods 298 of the first shift register 248. In this case, the first edge detection signal 278 only attains a high level at a time 321 that is a full clock cycle later than the time 305. This is because, due to the metastability of the first shift register 248, the rising edge of the event detection signal 256 is not accepted as an input until the rising edge 247 that occurs at the time 305, one clock cycle after the time 303 at which the shift register 248 accepted the input in FIG. 8. Because the time at which the first edge detection signal 278 is at a high level is delayed by one clock cycle relative to the corresponding time shown in FIG. 8, the 6-bit register 288 does not accept an updated value of the 6-bit count signal 238 until a time 323, such that the first output signal 289 attains a value of 000100 as opposed to 000011. Although not shown in FIG. 9, timing circuit 200 could behave in a similar fashion if the event detection signal 256 switched from a low level to a high level in one of the other metastable periods 300, 302 or 304. In such cases where the rising edge of the event detection signal 256 occurred in one of the respective metatstable periods 300, 302 or 304, the respective edge detection signals 280, 282 or 284 could be similarly delayed by a full clock cycle, causing a corresponding change in the output signals 291, 293 or 295.

None of this is to say that, just because the event detection signal 256 switches from a low level to a high level during one of the metastable periods 298–304, that any one of the respective edge detection signals 278–284 necessarily will be shifted by one clock cycle as shown in FIG. 9. Rather, when the shift registers 248–254 enter their respective metastable periods 298–304, it is possible either that the respective registers will require an additional clock cycle before a change in the event detection signal 256 is accepted as an input to the registers, or that the registers will not require the additional clock cycle.

Regardless of whether operation of the shift registers 248–254 in their respective metastable periods of operation in fact causes any of the respective edge detection signals 278–284 to be delayed by one cycle, the timing circuit 200 has the added benefit that, even if such operation in one of the metastable periods produces such a delayed edge detection signal, any change in the eventual overall output signal 296 will be limited to at most an error corresponding to only a single time period 325 (that is, at most an error corresponding to a 90 degree phase shift of one of the clock cycles). This is because, by providing the four different clock signals 218–224 as the clock inputs to the respective shift registers 248–254, the respective shift registers are staggered in terms of the times at which they will accept updated values of the event detection signal 256 as their input values. (The sum of the setup and hold time of the field programmable gate array on which the quadrature edge detection circuit is implemented is less than one time period 325.) Consequently, only one of the shift registers 248–254 at any given time can at that time be in its respective metastable period of operation 298–404 and produce a delayed edge detection signal pulse as a result.

For example, as shown in FIG. 9, only the first shift register 248 is delayed in accepting the new high level value of the event detection signal 256 due to the fact that the event detection signal switches during one of its respective metastable periods 298. Consequently, only the first edge detection signal 278 corresponding to that shift register 248 is then delayed in switching to its high level from the time 305 to the time 321. Further, only the portion of the overall output signal 296 that is related to the 6-bit count signal 238 is delayed by one clock cycle, and the final determination of the time ascribed to the detected event is only in error by an amount corresponding to the time period 325. This delay results in an error being introduced to the overall output signal 296 that corresponds to at most the one time period 325, namely an error of one count difference between the erroneous count 000100111 and the correct count 000011111.

Similarly, if the event detection signal 256 experienced its rising edge during one of the other metastable periods of time 300–304, and a respective one of the edge detection signals 280–284 was consequently shifted, this would introduce an error corresponding to one of the measured time periods 325. For example, if the event detection signal 256 switched at a time 327 during one of the metastable periods 300 corresponding to the second shift register 250, the respective edge detection signal 280 could be shifted one clock cycle past that shown in FIG. 9 such that the second output signal 291 would only attain a new value at a time 329. In such case, the error introduced would again be limited to an error corresponding to one measured time period 325, namely an error between an erroneous count 330 (000101110) and a correct count 333 (000101000). Additionally, because the timing circuit 200 limits the amount of error that can be introduced by metastability into the overall output signal 296 to an amount of error corresponding to at most one of the time periods 325, the timing circuit provides the further benefit that undefined count values do not occur in the overall output signal 296. For example, the timing circuit 200 avoids count values of the overall output signal 296 in which the lowest three bits of the count value take on the value 101. Such an erroneous value would only occur if one of the edge detection signals 278–284 was shifted more than one clock cycle due to the effects of metastability, something which the design of the timing circuit 200 precludes.

In alternate embodiments, the timing circuit 200 can take a variety of different forms. To begin, the quadrature clock 210 is intended to be representative of a variety of different clocks that implement one or more phase locked loop circuits to output, in addition to a first clock signal that varies at the clock frequency (e.g. the primary frequency), at least one or more additional clock signals that also vary at the primary frequency but are shifted in phase relative to the first clock signal. The clock need not be a quadrature clock producing four clock signals, but instead can be a clock providing any number of clock signals, and the various clock signals need not be equispaced in phase by 90 degrees or any other particular amount relative to one another. In such alternate embodiments, circuitry other than the inverters 215, 217 can be employed to provide desired phase shifts. Also, the primary frequency can vary from the frequency of 192 MHz discussed above.

With respect to the quadrature counter 226, the number of counter elements 228–234 need not, in alternate embodiments, include four separate counter elements. In most embodiments, the number of counter elements will correspond to the number of clock signals produced by the clock, although in certain embodiments this need not be the case. Further, different types of counter elements can be employed in place of the D type flip-flop counters 230–234 and the binary counter element 228, and the number of bits counted by each particular counter need not be identical to that shown, nor need the counter elements count bits in the manner shown. In particular, while the first counter element 228 is shown to be a 6-bit binary counter, in alternate embodiments, it can be a 5-bit counter or a ripple counter instead of a binary counter, for example. To the extent that the design of the counters changes, the nature and progression of the overall count signal 245 can also change.

With respect to the quadrature edge detection circuit 246, this circuit is meant to be exemplary of a variety of different types of status detection circuit that receive one or more clock signals and also received an event detection signal, and in response provide status signals indicative of whether the event detection signal has experienced particular status changes. Depending upon the embodiment, the number of shift registers 248–254, inverters 268–274 and AND gates 258–264 can vary from that shown particularly when a different number of clock signals is produced by the clock. Additionally, the number of bits of the shift registers 248–254 can be different than that of the 4-bit shift registers shown, although 4-bit shift registers have been chosen in the present embodiment because such shift registers are commonly available.

In the present embodiment shown in FIG. 7, each respective set of shift registers 248–254, inverters 268–274 and AND gates 258–264 can be said to form a respective status circuit that indicates whether the event detection signal 256 has undergone a status change from a low level to a high level. In alternate embodiments, different status circuits can be employed to detect different changes in the status of the event detection signal 256. For example, in one alternate embodiment the inverters 268–274 would be moved so that the inverters were in between the Q1 outputs of the shift registers 248–254 and the first inputs of the AND gates 258–264 instead of between the Q2 outputs of the shift registers and the second inputs the AND gates. In such an embodiment, the status circuits would detect falling edges of the event detection signal 256 rather than rising edges of that signal. Other embodiments would also be possible, either using the shift registers and other digital circuitry shown or a variety of other circuit elements, to detect other status changes or to provide related information. For example, in two alternate embodiments, the status circuits would detect changes in which the event detection signal 256 attained a high level or a low level for a particular period of time, or provide status signals indicative of how long the event detection signal 256 had remained at a particular level.

Finally, the quadrature count latch circuit 286 is meant to be representative of a variety of different circuits that can sample and then output upon the various sampled data. The exact storage elements used can vary from the registers 288–294 shown. In particular, the number and sizes of the different registers can vary depending upon the embodiment. For example, the 6-bit register 288 can be a 5-bit register if the first count signal 238 is a 5-bit count signal.

It should be apparent to those skilled in the art that many modifications may be made without departing from the spirit and scope of the invention.

What is claimed is:

1. For use in a medical imaging system, a timing circuit comprising:
   a clock having a primary frequency of operation, wherein the clock provides at least a first clock signal that varies at the primary frequency;
   a counter including first and second counter elements coupled to the clock, wherein the first counter element receives the first clock signal and in response provides a first count signal that varies at the primary frequency, and wherein the second counter element receives a second clock signal, and in response provides a second count signal;
   a status detection circuit including first and second status circuits coupled to the clock, wherein the first status circuit receives the first clock signal and an event detection signal and in response provides a first status signal indicative of whether the event detection signal has experienced a first status change, and wherein the second status circuit receives the second clock signal and the event detection signal and in response provides a second status signal indicative of whether the event detection signal has experienced the first status change; and
   an output circuit including first and second registers coupled to the clock and respectively coupled to the first and second counters and to the first and second status circuits, wherein the first and second registers respectively receive the first and second clock signals, the first and second count signals, and the first and second status signals, respectively, and in response respectively provide first and second output signals that collectively form an overall output signal indicative of a time at which the event detection signal experienced the first status change.

2. The timing circuit of claim 1, wherein the clock includes a phase locked loop circuit.

3. The timing circuit of claim 2, wherein the clock further includes an inverter coupled to the phase locked loop circuit, wherein the first clock signal is directly outputted by the phase locked loop circuit and is also provided to the inverter, which in turn outputs a second clock signal such that the second clock signal is 180 degrees out of phase with respect to the first clock signal.

4. The timing circuit of claim 2, wherein the clock further outputs second, third and fourth clock signals, wherein the clock further includes first and second inverters, wherein the phase locked loop circuit directly outputs the first and second clock signals such that the two respective signals are 90 degrees out of phase with one another, wherein the first and second clock signals are respectively provided to the first and second inverters, which in turn output the third and fourth clock signals such that the third clock signal is 90 degrees out of phase with the second clock signal and the fourth clock signal is 90 degrees out of phase with the third clock signal, and wherein the primary frequency is 192 MHz.

5. The timing circuit of claim 1, wherein the first counter element is a binary counter and the second counter element is a one-bit D flip-flop.

6. The timing circuit of claim 5, wherein the first clock signal is provided to a clock input of the binary counter and the second clock signal is provided to a clock input of the one-bit D flip-flop, wherein the one-bit D flip-flop receives at a D input a related signal, and wherein the related signal is a lowest bit of the first count signal that varies in value at the primary frequency.

7. The timing circuit of claim 6, wherein the binary counter is a 6-bit binary counter that further includes a reset input.

8. The timing circuit of claim 6, wherein the counter is a quadrature counter, wherein the clock further provides third and fourth clock signals that vary at the primary frequency, wherein the first, second, third and fourth clock signals are respectively at 0, 90, 180 and 270 degree phases relative to one another; and
   wherein the counter further includes third and fourth counter elements, each of which is a respective one-bit D flip-flop, wherein the third counter element receives the third clock signal at a clock input and the second count signal at a D input and in response provides a third count signal, and wherein the fourth counter element receives the fourth clock signal at a clock input and the third count signal at a D input and in response provides a fourth count signal.

9. The timing circuit of claim 1, wherein each of the first and second status circuits includes a respective shift register having an input and two outputs, a respective AND gate having two inputs and an output, and a respective inverter coupled between one of the inputs of the respective shift register and one of the inputs of the respective AND gate, wherein the other of the outputs of the respective shift register is directly coupled to the other of the respective inputs of the respective AND gate.

10. The timing circuit of claim 9, wherein each of the shift registers is a four-bit shift register.

11. The timing circuit of claim 9, wherein the status detection circuit is a quadrature edge detector that further comprises third and fourth status circuits, wherein each of the third and fourth status circuits includes a respective shift register having an input and two outputs, a respective AND gate having two inputs and an output, and a respective inverter coupled between one of the inputs of the respective shift register and one of the inputs of the respective AND gate, wherein the other of the outputs of the respective shift register is directly coupled to the other of the respective inputs of the respective AND gate.

12. The timing circuit of claim 9, wherein the first status signal changes from a first low value to a first high value upon an occurrence of a rising edge of the first clock signal when the event detection signal has changed from a second low value to a second high value prior to the occurrence of the rising edge of the first clock signal, and wherein the first status signal then remains at the first high value for a single period of the first clock signal and then returns to the first low value.

13. The timing circuit of claim 12, wherein the first status signal experiences a single-period delay prior to changing from the first low value to the first high value if the event detection signal changed from the second low level to the second high level during a metastable period.

14. The timing circuit of claim 9, wherein the first status signal changes from a first low value to a first high value upon an occurrence of a rising edge of the first clock signal when the event detection signal has changed from a second high value to a second low value prior to the occurrence of the rising edge of the first clock signal, and wherein the first status signal then remains at the first high value for a single period of the first clock signal and then returns to the first low value.

15. The timing circuit of claim 1, wherein the first status signal provided by the first status circuit changes from a first low value to a first high value upon an occurrence of a rising edge of the first clock signal when the event detection signal changes from a second low value to a second high value and remains at the second high value for a predetermined amount of time and then returns to the second low value.

16. The timing circuit of claim 1, wherein the first register sets the first output signal equal to a current value of the first count signal upon an occurrence of a rising edge of the first clock signal when the first status signal is at a high level indicating that the event detection signal has experienced the first status change, and wherein the second register sets the second output signal equal to a current value of the second count signal upon an occurrence of a rising edge of the second clock signal when the second status signal is at a high level indicating that the event detection signal has experienced the second status change.

17. The timing circuit of claim 1, wherein the timing circuit is implemented on a field programmable gate array.

18. The timing circuit of claim 1, wherein the timing circuit is configured for implementation on a medical imaging system selected from the group consisting of a PET scanner, an NMR scanner, and a CT scanner.

19. A PET scanner comprising:
    a plurality of detectors supported by a gantry;
    a plurality of acquisition circuits coupled to the detectors, wherein the acquisition circuits provide event detection signals that are related to signals received from detectors indicating that photons have been detected; and
    a plurality of event locator circuits that receive the event detection signals, wherein each event locator circuit includes
        a respective quadrature clock;
        a respective quadrature counter coupled to the respective quadrature clock;
        a respective quadrature edge detection circuit coupled to the respective quadrature clock and further coupled to at least one of the acquisition circuits to receive a respective one of the event detection signals; and
        a respective quadrature count latch circuit coupled to the respective quadrature clock, the respective quadrature counter and the respective quadrature edge detector,
    wherein the respective quadrature count latch circuit provides a respective output signal indicative of times at which the respective event detection signal undergoes transitions of a particular type, and
    wherein the respective quadrature edge detection circuit prevents the respective output signal from at least one of attaining values that are undefined and attaining values that are indicative of incorrect times that are more than one clock cycle in error relative to the times at which the respective event detection signal undergoes the transitions.

20. The PET scanner of claim 19, wherein in each event locator circuit:
    the respective quadrature clock includes a respective phase locked loop circuit that provides first, second, third and fourth clock signals that share the same frequency and are respectively at 0, 90, 180 and 270 degree phases relative to one another; and
    the respective quadrature counter includes first, second, third and fourth counter elements that respectively receive the first, second, third and fourth clock signals and output first, second, third and fourth count signals.

21. The PET scanner of claim 20, wherein in each event locator circuit:
    the respective quadrature edge detection circuit includes first, second, third and fourth edge detection elements that respectively receive the first, second, third and fourth clock signals and that additionally all receive the respective event detection signal,
    wherein the first, second, third, and fourth edge detection elements respectively output first, second, third and fourth edge detection signals that respectively attain high levels for single periods of the quadrature clock upon respectively determining that the respective event detection signal has undergone the particular type of transition, and
    wherein the first, second, third and fourth edge detection elements are respectively triggered to determine the transitions of the one event detection signal at rising edges of the first, second, third and fourth clock signals, respectively.

22. The PET scanner of claim 21, wherein in each event locator circuit:

the respective quadrature count latch circuit includes first, second, third and fourth registers that respectively receive the first, second, third and fourth clock signals, and are respectively coupled to the first, second, third and fourth edge detector elements and counter elements, wherein the first, second, third and fourth registers respectively store values of the first, second, third and fourth count signals only when the first, second, third and fourth edge detection signals are respectively at the high-levels and when the first, second, third and fourth registers are respectively triggered by the rising edges of the first, second, third and fourth clock signals, and wherein the first, second, third and fourth registers respectively output the stored values of the first, second, third and fourth count signals, which together form the output signal.

23. A timing circuit for implementation in a medical imaging device, the timing circuit comprising:

a phase locked loop circuit employed to generate at least two clock signals having the same frequency and each having a different phase relative to one another;

a means for providing a count signal based upon the at least two clock signals; and a means for associating and outputting a particular count of the count signal with a status change of an event detection signal, wherein the particular count is indicative of a time at which the status change occurred.

24. A method of ascribing times to events in a medical imaging system, the method comprising:

generating a plurality of clock signals at a phase locked loop circuit, wherein all of the clock signals have the same frequency but have different phases;

providing each clock signal to a respective counter element;

generating at each counter element a respective count signal, wherein the count signals together represent successive time increments, and wherein the time increments are smaller than a period of the clock signals;

providing an event detection signal and the plurality of clock signals to a plurality of status circuits, wherein each clock signal is provided to a respective status circuit;

determining at each status circuit, at times at which the respective clock signals change in their states, whether the event detection signal has undergone a particular status change;

generating at each status circuit a respective status signal, wherein each respective status signal attains a particular level whenever the respective status circuit determines that the event detection signal has undergone the particular status change;

receiving at respective storage elements the respective clock signals, status signals and count signals;

storing values of the respective count signals in the respective storage elements at times when respective clock signals change in their states and when the respective status signals have attained the particular level; and outputting the stored values, as an overall output signal that indicates times at which the event detection signal has undergone the particular status change.

* * * * *